United States Patent [19]

Mobilio

[11] Patent Number: 4,886,826

[45] Date of Patent: Dec. 12, 1989

[54] SUBSTITUTED 2,3,4,9-TETRAHYDRO-1H-CARBAZOLE-1-ACETIC ACID DERIVATIVES, COMPOSITION AND USE

[75] Inventor: Dominick Mobilio, Franklin Park, N.J.

[73] Assignee: American Home Products Corporation, New York, N.Y.

[21] Appl. No.: 359,560

[22] Filed: Jun. 1, 1989

[51] Int. Cl.⁴ .................... A61K 31/40; C07D 209/86
[52] U.S. Cl. ..................................... 514/411; 548/439
[58] Field of Search ......................... 548/439; 514/411

[56] References Cited

U.S. PATENT DOCUMENTS

| | | |
|---|---|---|
| 4,584,312 | 4/1986 | Mobilio et al. ................ 514/411 |
| 4,616,028 | 10/1986 | Mobilio et al. ................ 514/411 |
| 4,687,860 | 8/1987 | Mobilio et al. ................ 514/411 |

Primary Examiner—Robert W. Ramsuer
Attorney, Agent, or Firm—Walter Patton

[57] ABSTRACT

Substituted 2,3,4,9-tetrahydro-1H-carbazole-1-acetic acid derivatives and methods for their preparation and use are disclosed. The compounds are useful analgesic, anti-inflammatory, anti-asthmatic and anti-allergic agents.

5 Claims, No Drawings

SUBSTITUTED 2,3,4,9-TETRAHYDRO-1H-CARBAZOLE-1-ACETIC ACID DERIVATIVES, COMPOSITION AND USE

BACKGROUND OF THE INVENTION

This invention relates to novel tetrahydrocarbazole acetic acid derivatives possessing lipoxygenase inhibitory and/or cyclooxygenase inhibitory activity which are useful as anti-inflammatory and antiallergic agents. For instance, they exhibit analgesic and anti-inflammatory activity at dose levels which do not elicit undesirable side effects. The foregoing combination of attributes render the compounds of this invention useful for the treatment of inflammatory conditions and of pain and allergy.

It is known that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$, $D_4$ and $E_4$. The substance denominated slow-reacting substance of anaphylaxis (SRS-A) has been shown to consist of a mixture of sulfidopeptide leukotrienes, $C_4$, $D_4$ and $E_4$ [see Back et al, J. Immun., 215, 115–118 (1980); Biochem. Biophys. Res. Commun. 93, 1121–1126(1980)].

The significance of these leukotrienes is that a great deal of evidence has been accumulated showing the leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi[see Dahlen et al, Nature, 288, 484–486 (1980) and piper, Int. Arch. Appl. Immunol., 76, suppl. 1, 43 (1985)] which stimulate the release of mucus from airways in vitro [Marom et al, Am. Rev. Resp. Dis., 126, 449 (1982)], are potent vasodilators in skin [see Bisgaard et al, Prostaglandins, 23, 797 (1982)], and produce a wheal and flare response [Camp et al, Br. J. Pharmacol., 80, 497 (1983)]. The nonpeptide leukotriene, $LTB_4$, is a powerful chemotactic factor for leukocytes [see A. W. Ford-Hutchinson, J. Roy. Soc. Med., 74, 831–833 (1981)], which stimulates cell accumulation and affects vascular smooth muscle [see Bray, Br. Med. Bull., 39, 249 (1983)]. The activity of leukotrienes as mediators of inflammation and hypersensitivity is extensively reviewed in Bailey and Casey, Ann. Reports Med. Chem., 17, 203–217 (1982) and in Bray, Agents and Actions, 19, 87 (1986).

Accordingly, the biological activity of the leukotrienes and SRS-A's, and of lipoxygenase as the enzyme leading to the metabolism of AA to leukotrienes, indicates that a rational approach to drug therapy to prevent, remove, or ameliorate the symptoms of allergies, anaphylaxis, asthma and inflammation must focus on blocking the release of mediators of these conditions. Thus, compounds which control the biosynthesis of the leukotrienes and SRS-A's by inhibiting lipoxygenase, are considered to be of value in treating such conditions as allergic bronchial asthma, allergic rhinitis, as well as in other immediate hypersensitivity reactions.

FIELD OF INVENTION

This invention relates to tricyclic acetic acid derivatives, to their preparation and use, and to intermediates used for their preparation.

More specifically, this invention relates to tricyclic acetic acid derivatives in which the tricyclic portion thereof is characterized by having an indole portion fused to a cyclohexane ring. Still more specifically, the compounds of this invention are characterized as derivatives of the following tricyclic acetic acid system:

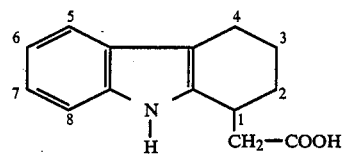

2,3,4,9-tetrahydro-1H-carbazole-1-acetic acid in which the carbons at the 1-, 4-, 5-, 6-, 7- and 8-positions are further substituted.

The tricyclic acetic acid compounds of this invention possess useful pharmacologic properties; for instance, they exhibit analgesic and anti-inflammatory activity at dose levels which do not elicit undesirable side effects. The foregoing combination of attributes renders the compounds of this invention useful for the treatment of inflammatory or painful conditions in a mammal or as anti-asthmatic or antiallergic agents.

PRIOR ART

The closest prior art to the present invention is:

U.S. Pat. Nos. 4,616,028; 4,584,312; 4,578,398; 4,687,860; 4,701,533 and 4,709,048.

Demerson et al, U.S. Pat. No. 3,939,178 discloses 1,3,4,9-tetrahydropyrano[3,4-b]indoles and 1,3,4,9-tetrahydrothiopyrano[3,4-b]indoles having analgesic and anti-inflammatory activity.

Boehringer Mannheim European Patent 42593 generically discloses starting materials useful for producing cardiotonic and beta-blocking agents. The starting materials include 1,2,3,4-tetrahydrocarbazoles with substituents selected from the broad group including hydrogen, carboxy, lower alkyl and lower alkenyl. The starting materials are in each case also substituted with a reactive group which distinguishes them from the compounds of the present invention.

SUMMARY OF THE INVENTION

The anti-inflammatory, analgesic, anti-asthmatic and anti-allergic compounds of this invention are represented by formulas (I) and (II)

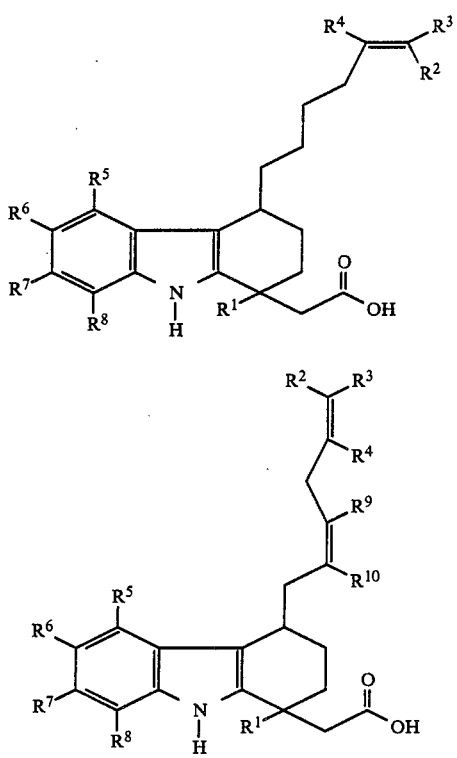

wherein $R^1$ is lower alkyl and $R^2$, $R^3$ and $R^4$ are independently H, lower alkyl or $R^3$ and $R^4$ are joined to form.

or $(CH_2)_n$ wherein n is 3 to 5 $R^5$, $R^6$, $R^7$ and $R^8$ are independently H, lower alkyl, halogen, haloalkyl; $R^9$ and $R^{10}$ are independently H, lower alkyl or $R^9$ and $R^{10}$ are joined to form

or $(CH_2)_m$ wherein m is 3 to 5 or the pharmaceutically acceptable salts thereof.

A preferred aspect of this invention is represented by formula (I) and (II) wherein $R^1$ is ethyl, $R^2$, $R^3$, $R^4$, $R^5$, $R^6$, $R^7$, $R^9$, and $R^{10}$ are hydrogen; $R^8$ is methyl or ethyl or the pharmaceutically acceptable salts thereof.

The most preferred compounds of the present invention are 1,8-diethyl-4-(5-hexenyl)-2,3,4,9-tetrahydro-1H-carbazole-1-acetic acid;

1-ethyl-4-(5-hexenyl)-2,3,4,9-tetrahydro-8-methyl-1H-carbazole-1-acetic acid (Isomer B);

1-ethyl-4-(5-hexenyl)-2,3,4,9-tetrahydro-8-methyl-1H-carbazole-1-acetic acid (Isomer A);

[1α,4α(Z)]-1-ethyl-4-(2,5-hexadienyl)-2,3,4,9-tetrahydro-8-methyl-1H-carbazole-1-acetic acid;

or the pharmaceutically acceptable salts thereof.

The compounds of the present invention represented by formula (I) are prepared by a process in which the unsaturated ketone of structure (III),

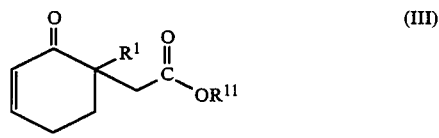

prepared as described by Mobilio et al, in U.S. Pat. No. 4,578,398, wherein $R^1$ is as defined above and $R^{11}$ is lower alkyl is reacted in the presence of a suitable copper catalyst selected from the group consisting of copper bromide dimethyl sulfide complex, cuprous iodide, cuprous bromide, copper acetate, cuprous chloride and tributylphosphine cuprous iodide complex, with the organometallic reagent

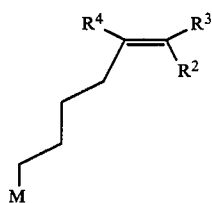

wherein $R^2$, $R^3$ and $R^4$ are as defined above and M may be MgBr, MgCl or MgI to obtain a compound of structure (IV)

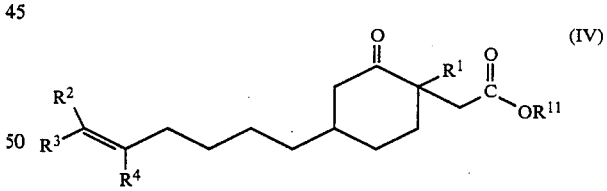

wherein $R^1$, $R^2$, $R^3$, $R^4$ and $R^{11}$ are as defined above and further reacting a compound of structure (IV) with the substituted hydrazine of formula (V)

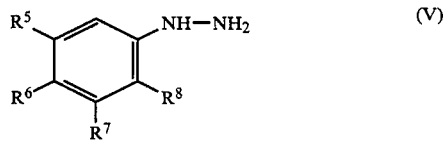

wherein $R^5$, $R^6$, $R^7$ and $R^8$ are as defined above to obtain the corresponding hydrazone of structure (IV)

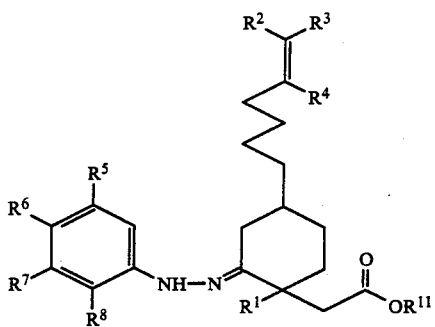

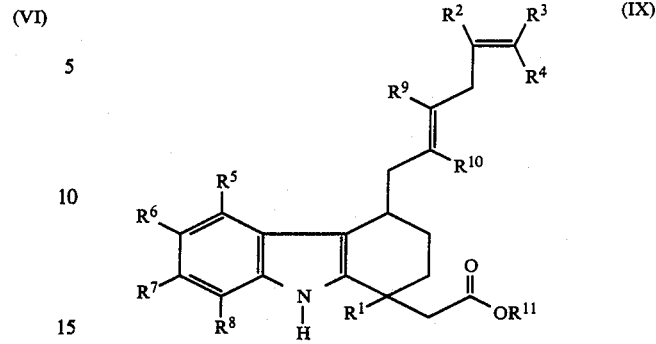

wherein $R^1$, $R^2$, $R^3$, $R^4$, $R^5$, $R^6$, $R^7$, $R^8$ and $R^{11}$ are as defined above. The hydrazone is treated with a cyclizing agent to give the ester of compound (I) and after hydrolyzing compound (I) is obtained.

The compounds of the present invention represented by formula (II) wherein $R^9$ and $R^{10}$ are not joined to form

or $(CH_2)_m$, can be prepared by a process in which the tetrahydrocarbazole of structure (VII)

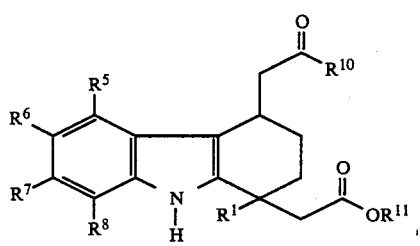

prepared as described by Mobilio et al, in U.S. Pat. No. 4,701,533, wherein $R^1$, $R^5$, $R^6$, $R^7$, $R^8$ and $R^{11}$ are as defined above is reacted with a compound of structure (VIII)

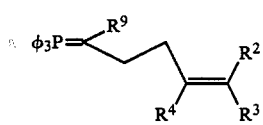

wherein $R^2$, $R^3$, $R^4$ and $R^9$ are as defined above, to produce the ester of a compound of formula (II) or a mixture of the ester of compounds of formula (II) and formula (IX)

from which a compound of formula (II) can be isolated by classical separation techniques which include recrystallization and chromatography. In the case where $R^9$ and $R^{10}$ are hydrogen, the ester of the compound of formula (II) can be produced in substantially pure form, free from large quantities of a compound of formula (IX). After hydrolyzing the ester of formula (II), the compound of formula (II) is obtained.

The compounds of the present invention represented by formula (II) wherein $R^9$ and $R^{10}$ are joined to form

or $(CH_2)_m$ wherein m is 3 to 5 are prepared by a process in which the unsaturated ketone of structure (III),

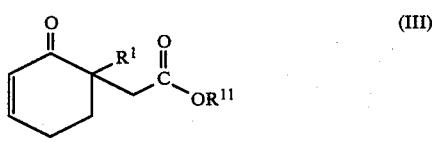

prepared as described by Mobilio et al, in U.S. Pat. No. 4,578,398, wherein $R^1$ and $R^{11}$ are defined above, is reacted in the presence of a suitable copper catalyst selected from the group consisting of copper bromide dimethyl sulfide complex, cuprous iodide, cuprous bromide, copper acetate, cuprous chloride and tributylphosphine cuprous iodide complex, with the organometallic reagent

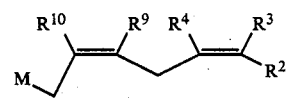

wherein $R^2$, $R^3$, $R^4$, $R^9$ and $R^{10}$ are as defined above and M may be MgBr, MgCl or MgI to obtain a compound of structure (X)

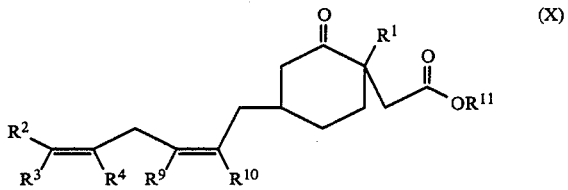

wherein $R^1$, $R^2$, $R^3$, $R^4$, $R^9$, $R^{10}$ and $R^{11}$ are as defined above and further reacting a compound of structure (X) with the substituted hydrazine of formula (V)

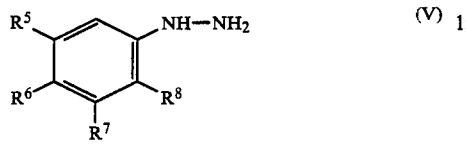

wherein $R^5$, $R^6$, $R^7$ and $R^8$ are as defined above to obtain the corresponding hydrazone of structure (XI)

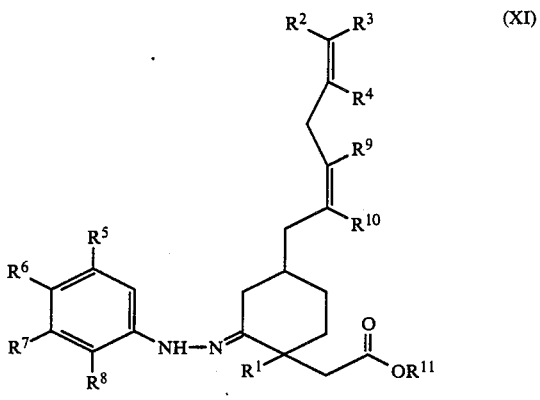

wherein $R^1$, $R^2$, $R^3$, $R^4$, $R^5$, $R^6$, $R^7$, $R^8$, $R^9$, $R^{10}$ and $R^{11}$ are as defined above. The hydrazone is treated with a cyclizing agent to give the ester of compound (II) and after hydrolyzing, compound (II) is obtained.

Generally speaking, the condensation of (IV) and (V) or (X) and (V) is performed preferably in an inert atmosphere, for example, nitrogen or argon. Suitable solvents for the condensation include the lower alkanols such as methanol and ethanol; aromatics such as benzene and toluene; the ethers, such as tetrahydrofuran, diethyl ether, dioxane, bis(2-methoxyethyl)-ether and the like; and the halogenated hydrocarbons, methylene chloride, chloroform and the like. Methanol and ethanol are especially convenient and practical solvents. Times and temperatures for the condensation generally range from 5 minutes to five or six days at 0° to 100° C. Convenient time and temperature ranges include 20° C. to the boiling point of the mixture and 15 minutes to 130 hours.

The resulting hydrazones (VI) or (XI) are then cyclized to the tricyclic ester of the acid of formula (I) or (II) by the action of a suitable cyclization agent according to the conditions of the "Fischer Indole Synthesis," for example, see B. Robinson, Chem. Rev. 63, 373 (1963).

A variety of cyclization agents are effective for this cyclization, some of the agents suitable for this cyclization include p-toluenesulfonic acid, hydrogen chloride or hydrogen chloride generated from acetyl chloride, hydrogen bromide, phosphoric acid, sulfuric acid, aluminum chloride, zinc chloride, hydrogen bromide in acetic acid, boron trifluoride-etherate, trifluoroacetic acid, cationic ion exchange resins such as Amberlite IR-120, phenyl or ethyl magnesium bromide and aniline salts. In other words the usual catalysts employed for the "Fischer Indole Synthesis" are efficacious; however, the preferred cyclization agents are borontrifluoride etherate in acetic acid.

In practice the isolation of the hydrazone (VI) or (XI) from the condensation reaction mixture is optional. Accordingly, the cyclization agent is added either to the above condensation reaction mixture containing the hydrazone, or to the isolated hydrazone optionally dissolved in one of the above solvents, whereby the hydrazone then cyclizes to give the corresponding tricyclic ester of formula (I) or (II).

The cyclization usually proceeds smoothly and rapidly. Convenient reaction times for the cyclization include five minutes to two hours, preferably 30 minutes to one hour. Convenient temperatures include 20° to 200° C., preferably 120° to 180° C.

In practice a most convenient and practical procedure for effecting the above cyclization comprises evaporating solvent from the condensation reaction mixture containing the hydrazone, and then heating the hydrazine at 120° to 200° C. in one of the aforementioned solutions of strong acids.

The subsequent conversion of the lower alkyl ester tricyclic compound of formula (I) or (II) to the corresponding compound of formula (I) or (II) is effected readily by subjecting the tricyclic compound to hydrolysis. Generally speaking, this conversion is most conveniently performed by employing a base as the hydrolyzing agent. The hydrolysis is performed in the presence of sufficient water optionally under an inert atmosphere, followed by acidification of the reaction mixture to yield the desired compound of formula (I) or (II). However, the manner of hydrolysis is not intended to be limited to basic hydrolysis since hydrolysis under acidic conditions and other variations, for example, treatment with lithium iodide in collidine (see L. F. Fieser and M. Fieser, "Reagents for Organic Synthesis," John Wiley and Sons, Inc., New York, 1967, pp. 615–617) are also applicable.

For basic hydrolysis a preferred embodiment involves subjecting the tricyclic ester to the action of a base, for example, sodium or potassium carbonate, in the presence of sufficient water to effect hydrolysis of the ester. The hydrolysis is performed using a suitable solvent, for example, methanol or ethanol under a nitrogen atmosphere.

The reaction mixture is maintained at a temperature of from 25° C. to the reflux temperature until hydrolysis occurs. Usually from 10 minutes to 48 hours is sufficient for this hydrolysis. The reaction is then rendered acidic with an acid, for example, acetic acid, hydrochloric acid, sulfuric acid and the like, to release the free acid as a solid.

Alternatively, the tricyclic ester is hydrolyzed by subjecting the ester to the action of a hydrolyzing agent which is a strong organic or inorganic acid, for example, trifluoroacetic acid, p-toluenesulfonic acid, hydrochloric acid, hydrobromic acid, hydroiodic acid, sulfuric acid, phosphoric acid and the like in a suitable solvent at a temperature of at least 60° C. and preferably from 90° C. to the boiling point of the mixture until the hydrolysis occurs. Usually from 5 to 48 hours are required for this hydrolysis. Suitable solvents include water, acetic acid, aqueous alcohols and the like. If acid hydrolysis is used, the free acid is formed directly. If necessary, the reaction mixture can be diluted with water to precipitate the product.

DETAILED DESCRIPTION OF THE INVENTION

The term "lower alkyl" as used herein contemplates straight chain alkyl radicals containing from one to six carbon atoms and branched chain alkyl radicals containing from three to four carbon atoms and includes methyl, ethyl, propyl, isopropyl, butyl, isobutyl, pentyl, hexyl and the like.

The term "halogen" as used herein includes fluorine, chlorine, bromine and iodine.

The compounds of formula (I) or (II) form salts with suitable pharmaceutically acceptable inorganic and organic bases. These derived salts possess the same activity as the parent acid and are included within the scope of this invention. The acid of formula (I) is transformed in excellent yield into the corresponding pharmaceutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like; mono, di- and trialkanolamines, the alkanol radicals of which contain up to three carbon atoms, such as mono-, di- and triethanolamine; tris(hydroxymethyl)-aminomethane; alkylenediamines which contain up to six carbon atoms, such as hexamethylenediamine; amino sugars, such as glucosamine; phenyl substituted alkylamines, such as benzenemethanamine or N,N-bis-(phenylmethyl)-1,2-ethanediamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example the N-methyl-pyridinium, N-methyl-N-(2-hydroxyethyl)-morpholinium, N,N-dimethyl-morpholinium, N-methyl-N-(2-hydroxyethyl)-morpholinium, N,N-dimethylpiperidinium salts, which are characterized by good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula (I) or (II) in water containing at least one equivalent amount of a hydroxide, carbonate, or bicarbonate corresponding to the inorganic salt desired. Advantageously, the reaction is performed in a water-miscible organic solvent inert to the reaction conditions, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acid of formula (I) or (II) is dissolved in a suitable solvent of either moderate or low polarity, for example, ethanol, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) or (II) with an equivalent amount of the corresponding quaternary ammonium hydroxide in water solution, followed by evaporation of the water.

Included in the present invention are the diastereoisomers wherein the 4-substituent is either cis or trans to the acetic acid chain at position one.

Also included in this invention are the optical isomers of the compounds of formula (I) or (II) which result from asymmetric centers, contained therein. Such isomers are obtained in substantially pure form by classical separation techniques and by sterically controlled synthesis.

The compounds of the invention, by virtue of their ability to inhibit the activity of lipoxygenase enzyme and/or cyclooxygenase enzyme are useful in the treatment of inflammatory and painful conditions. Accordingly, the compounds are indicated in the treatment of such diseases as rheumatoid arthritis, osteoarthritis, tendinitis, bursitis and similar conditions involving inflammation. Moreover, by virtue of their ability to inhibit the activity of lipoxygenase enzyme they are useful for the inhibition of symptoms induced by leukotrienes. Accordingly, the compounds are indicated in the prevention and treatment of those disease states in which $LTC_4$, $LTD_4$ and $LTE_4$ are causative factors, for example allergic rhinitis, allergic bronchial asthma and other leukotriene mediated naso-bronchial obstructive air-passageway conditions, as well as in other immediate hypersensitivity reactions, such as allergic conjunctivitis. The compounds are especially valuable in the prevention and treatment of allergic bronchial asthma.

When the compounds of the invention are employed in the treatment of allergic airway disorders and/or as anti-inflammatory agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least sufficient to impart the desired activity thereto an oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day. These effective concentration levels are usually obtained within a therapeutic range of 1.0 mg to 500 mg/kg per day, with a preferred range of 10 mg to 100 mg/kg per day.

The lipoxygenase inhibitory effects as well as the anti-inflammatory effects of the compounds of the invention may be demonstrated by standard pharmacological procedures, which are described more fully in the examples given hereinafter.

ANTI-INFLAMMATORY ACTIVITY

The useful anti-inflammatory activities of the tetrahydrocarbozole acetic acid derivatives of formula (I) and (Ia) are demonstrated in standard pharmacologic tests, for example, the test designated: Preventative Adjuvant Edema The objective of this test is to determine the ability of test drugs to exhibit an acute anti-inflammatory effect in rats. This test is a primary screen for anti-inflammatory drugs.

Species

Male Sprague Dawley rats (180–200 g) are used. The animals have free access to water but food is withdrawn 18 hours before testing.

Drug Preparations and Administration

Freund's complete adjuvant is prepared by suspending 5 mg of killed and dried *Mycobacterium butyricum* (Difco) in 1 mL liquid paraffin. The test compounds are dissolved in distilled water or suspended in 0.5% Tween 80 in distilled water according to their solubility. For primary screening all drugs are administered by gastric gavage at the arbitrary dosage of 25 mg/kg, p.o. in a volume of 0.5 mL/100 g body weight to groups of 10 animals.

Methodological Details

The method is essentially that described by Wax et al, J. Pharmacol. Exp. Ther., 192, 166–171 (1975). Groups of rats are injected intradermally in the left hind paw with 0.1 mL of Freund's complete adjuvant. The test compound or vehicle is administered immediately before the adjuvant, 24 hours and 48 hours after the adjuvant (days 0, 1 and 2). The injected hind paw volume is measured before the injection of adjuvant and 24 hours after the last drug administration (day 3) by means of a plethysomometer (Buxco Electronics Inc.). The difference between the hind paw volume on day 0 and day 3 represents the edema volume. Etodolac (25 mg/kg, p.o.) is included as a positive control.

Presentation of Results

The mean edema volume (expressed as mL±SEM) is calculated for each group and the percentage inhibition of inflammation conferred by the drug is calculated:

$$\% \text{ inhibition} = \left[ \frac{(c - t)}{c} \right] \times 100$$

where c is the mean edema volume for the untreated controls and t is the mean edema volume for the drug treated group.

ANALGESIC ACTIVITY

A further test used to determine the utility of the compounds of the present invention is designated: Drug Effects on Phenylbenzoquinone-induced Writhing in Mice.

The objective of this test is to determine the ability of test drugs to inhibit the nociceptive (pain) response of mice injected with a chemical irritant. This test is a primary screen for both peripherally and centrally acting analgesic drugs.

Species

Male Swiss albino mice (15–25 g) are used. The animals are fasted for 18 hours prior to use but have free access to water.

Drug Preparation and Administration

Drugs are dissolved or suspended according to their solubility in 0.5% Tween 80 in distilled water. They are administered by gastric gavage in a volume of 5 mL/kg. For primary screening all drugs are administered at the arbitrary dosage of 10 mg/kg, p.o. to a group of 10 mice.

Methodological Details

A modification of the method of Siegmund et al., Proc. Soc. Exp. Biol. Med., 95, 729–731 (1957) is used. Groups of 5 mice are dosed with the test compound or vehicle control. Sixty minutes later the animals are injected i.p. with 0.3 mL/20 g body weight of a 0.02% solution of phenylbenzoquinone (PBQ; 2-phenyl-1,4-benzoquinone) and placed in individual observation boxes. The number of writhes or abdominal squirming movements made by each mouse during the following 15 minute period is counted. The experiment is repeated with another group of 5 mice and the mean number of writhes per mouse for a group of 10 mice is calculated.

Presentation of Results

Drug-treated and vehicle-treated control groups are compared and the percentage protection conferred by the drug is calculated:

$$\text{Percentage protection} = \frac{(c - t) \, 100}{c}$$

where c=mean number of writhes in the control group
where t=mean number of writhes in the test drug group A test for lipoxygenase and cyclooxygenase inhibitory activity is the Rat Polymorphonuclear Leukocyte Assay. The assay is carried out as follows: glycogen-elicited rat peritoneal cells ($10^7$/1.0 mL) are incubated (37° C.)±drug in a shaking water bath for 10 minutes. One micromolar (final concentration) $^3$H arachidonic acid (2.0 μCi) is then added to each sample followed by the immediate addition of 1.0 micromolar A23187* (final concentration). The cells are incubated another 10 minutes and the reaction is stopped by high-speed centrifugation. Supernatants are then analyzed by HPLC using an in-line radioactivity detector. Effective drugs demonstrate a reduction in the integrated value of a given eicosanoid peak. Results are qualitatively expressed as a percent change (minus=decrease, plus=increase) relative to the control (no drug).

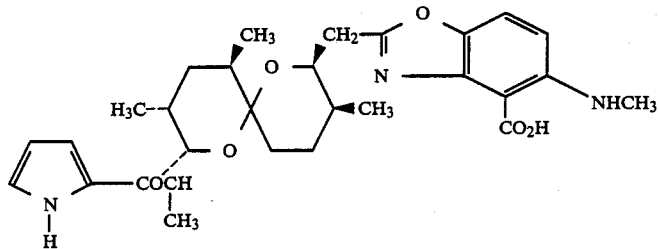

*A23187

Typical results obtained for the compounds of the present invention in the aforementioned tests are as follows:

Preventative Adjuvant Edema

| Compound | Dose (mg/kg, p.o.) | % Inhibition |
|---|---|---|
| Example 1 | 25 | 0 |
| Example 2 | 25 | 28 |
| Example 3 | 25 | 19 |
| Example 4 | 25 | 43 |

Phenylbenzoquinone Writhing in Mice

| Compound | Dose (mg/kg, p.o.) | % Inhibition |
|---|---|---|
| Example 1 | 10 | 0 |
| Example 2 | 10 | 0 |
| Example 3 | 10 | 10 |
| Example 4 | 10 | 23 |

Rat Polymorphonuclear Leukocyte Assay
% change at 10 μM drug concentration

| | leukotriene B4 | 5-HETE* | thromboxane B2 | prostaglandin E2 |
|---|---|---|---|---|
| Example 1 | −93 | −92 | −82 | −31 |
| Example 2 | −95 | −92 | −80 | +22 |
| Example 4 | −94 | −94 | −88 | −19 |

*5-hydroxyeicosatetraenoic acid

The lack of side effects for the compounds of this invention are demonstrated by standard acute toxicity tests described by R. A. Turner in "Screening Methods in Pharmacology," Academic Press, New York and London, 1965, pp. 152–163 and by prolonged administration of the compound to warm-blooded animals.

When the compounds of this invention are employed as anti-inflammatory and analgesic agents in warm-blooded animals, they are administered orally, alone or in dosage forms, i.e., capsules or tablets, combined with pharmacologically acceptable excipients, such as starch, milk sugar and so forth, or they are administered orally in the form of solutions in suitable vehicles such as vegetable oils or water. The compounds of this invention may be administered orally in sustained release dosage form or transdermally in ointments or patches. The compounds of this invention may also be administered in the form of suppositories.

The dosage of the compounds of formula I of this invention will vary with the particular compound chosen and form of administration. Furthermore, it will vary with the particular host under treatment. Generally, the compounds of this invention are administered at a concentration level that affords protective effects without any deleterious side effects. These anti-inflammatorily effective concentration levels are usually obtained within a therapeutic range of 1.0 μg to 500 mg/kg per day, with a preferred range of 10 μg to 100 mg/kg per day.

The compounds of this invention also possess antipyretic activity.

The compounds of this invention may be administered together with the usual doses of caffeine.

The following examples further illustrate this invention.

EXAMPLE 1

1,8-Diethyl-4(5-hexenyl)-2,3,4,9-tetrahydro-1H-carbazole-1-acetic Acid

Step (1) Preparation of 1-Ethyl-4-(5-hexenyl)-2-oxocyclohexaneacetic Acid Methyl Ester A solution of 1-ethyl-2-oxocyclohex-3-eneacetic acid methyl ester (25 g, 127.6 mmol), CuBr.Me$_2$S (2.62 g, 12.8 mmol) and Me$_2$S (25.5 mL) in 375 mL of tetrahydrofuran was cooled to −40° C. under nitrogen and treated dropwise with H$_2$C=CHCH$_2$CH$_2$CH$_2$CH$_2$MgBr (166.6 mmol, 303 mL of a 0.55M solution in tetrahydrofuran). Fifteen minutes after the addition, the reaction mixture was quenched with 300 mL of 1M HCl and extracted with 4×120 mL of ether. Drying (MgSO$_4$), concentration in vacuo and flash chromatography (114 mm diameter column, 10% ethyl acetate in petroleum ether eluent) afforded the oily product (29.51 g, 105.4 mmol, 83%) as a mixture of diastereomers. A portion of the diastereomers was separated by preparative HPLC affording 2.25 g of isomer A, the higher $R_f$ material, as a yellow oil.

$^1$H NMR (CDCl$_3$, 200 MHz): δ 0.8 (t, 3H), 1.4–2.7 (m, 19H), 3.65 (s, 3H), 4.9–5.1 (m, 2H), 5.7–5.9 (m, 1H)

and 8.3 g of isomer B, the lower $R_f$ material, as a yellow oil $^1$H NMR (CDCl$_3$, 200 MHz): δ 0.8 (t, 3H), 1.2–2.7 (m, 19H), 3.63 (s, 3H), 4.9–5.1 (m, 2H), 5.7–5.9 (m, 1H).

Step (2) Preparation of 1,8-Diethyl-4-(5-hexenyl)-2,3,4,9-tetrahydro-1H-carbazole-1-acetic Acid A solution of 1-ethyl-4-(5-hexenyl)-2-oxocyclohexaneacetic acid methyl ester isomer B (4.24 g, 15.14 mmol) and 2-ethylphenylhydrazine (2.27 g, 16.7 mmol) in 30.3 mL of toluene was refluxed under nitrogen for 22 hours with azeotropic removal of water. The toluene was then removed in vacuo and replaced with 10.8 mL of acetic acid. The solution was treated with borontrifluoride etherate (2.79 g, 19.7 mmol, 2.42 mL) and refluxed for 20 minutes under nitrogen. The reaction mixture was poured into 120 mL of water and extracted with 4×80 mL of 2.5N NaOH. Drying (MgSO$_4$) and flash chromatography (75 mm diameter column, 8% ethyl acetate in petroleum ether eluent) afforded 3.72 g (9.73 mmol, 64%) of 1,8-diethyl-4-(5-hexenyl)-2,3,4,9-tetrahydro-1H-carbazole-1-acetic acid methyl ester. Of this, 3.68 g (9.66 mmol) were refluxed in a solution of ethanol (30.9 mL) and 2.5N NaOH (7.7 mL) for 45 minutes under nitrogen. The ethanol was then removed in vacuo and the residue was suspended in 120 mL of 1N HCl. It was extracted with 4×40 mL of ether and the pooled extracts were dried over MgSO$_4$. Flash chromatography (50 mm diameter column, 10% ethyl acetate in petroleum ether eluent, 2% H$_3$PO$_4$ in MeOH treated silica gel) afforded 3.41 g (9.18 mmol, 95%) of a light yellow solid which was recrystallized from 85:15 petroleum ether:benzene. This resulted in 1.98 g of a white powder which were dried at 84° C. for 31 hours followed by recrystallization from 85:15 petroleum ether:benzene once again. Drying at 84° C. for 24 hours resulted in 1.41 g of a white powder, m.p. 96°–97° C.

$^3$H NMR (CDCl$_3$, 400 MHz): δ 0.89 (t, 3H, J=7.5 Hz), 1.34 (t, 3H, J=7.6 Hz), 1.4–2.1 (m, 14H), 2.75 (s, 2H), 2.83 (q, 2H, J=7.6 Hz), 2.9–3 (m, 1H), 4.9–5.16 (m, 2H), 5.78–5.9 (m, 1H), 6.96 (d, 1H, J=7.0 Hz), 7.01 (t, 1H, J=7.5 Hz), 7.41 (d, 1H, J=7.6 Hz), 8.93 (s, 1H)

Anal. Calcd. for C$_{24}$H$_{33}$NO$_2$: C, 78.43; H, 9.05; N, 3.81; Found: C, 78.11; H, 8.76; N, 3.88.

EXAMPLE 2

1-Ethyl-4-(5-hexenyl)-2,3,4,9-tetrahydro-8-methyl-1H-carbazole-1-acetic Acid (Isomer B)

The title compound was prepared from 1-ethyl-4-(5-hexenyl)-2-oxocyclohexaneacetic acid methyl ester (isomer B) and 2-methylphenylhydrazine as described in Example 1, m.p. 111°–112° C.

$^1$H NMR (CDCl$_3$, 400 MHz): δ 0.91 (t, 3H, J=7.5 Hz), 1.4–2.14 (m, 14H), 2.47 (s, 3H), 2.77 (s, 2H), 2.9–3 (m, 1H), 4.94–5.06 (m, 2H), 5.8–5.9 (m, 1H), 6.94 (d, 1H, J=6.7 Hz), 7.00 (t, 1H, J=7.4 Hz), 7.42 (d, 1H, J=7.7 Hz), 8.90 (s, 1H)

IR (KBr, cm$^{-1}$): 3420, 3080, 3050, 2930, 2860, 1700

Anal. Calcd. for C$_{23}$H$_{31}$NO$_2$: C, 78.15; H, 8.84; N, 3.96; Found: C, 77.83; H, 8.56; N, 4.00.

EXAMPLE 3

1-Ethyl-4-(5-hexenyl)-2,3,4,9-tetrahydro-8-methyl-1H-carbazole-1-acetic Acid (Isomer A)

The title compound was prepared from 1-ethyl-4-(5-hexenyl)-2-oxocyclohexaneacetic acid methyl ester (isomer A) and 2-methylphenylhydrazine as described in Example 1, m.p. 110°–111° C.

$^1$H NMR (CDCl$_3$, 400 MHz): δ 0.87 (t, 3H, J=7.4 Hz), 1.4–2.1 (m, 14H), 2.45 (s, 3H), 2.7 (d, 1H, J=16.3 Hz), 2.8 (d, 1H, J=16.4 Hz), 2.9–3 (m, 1H), 4.9–5.04 (m, 2H), 5.78–5.88 (m, 1H), 6.93 (d, 1H, J=6.1 Hz), 6.98 (t, 1H, J=7.4 Hz), 7.38 (d, 1H, J=7.8 Hz), 8.70 (s, 1H)

IR (KBr, cm$^1$): 3400, 3070, 2970, 2930, 2860, 1705, 1690

Anal. Calcd. for C$_{23}$H$_{31}$NO$_2$: C, 78.15; H, 8.84; N, 3.96; Found: C, 78.10; H, 8.59; N, 4.05.

EXAMPLE 4

[1, 4 (Z)]-1-Ethyl-4-(2,5-hexadienyl)-2,3,4,9-tetrahydro-8-methyl-1H-carbazole-1-acetic Acid 4-Butenyl-triphenylphosphonium iodide (6.21 mmol, 2.76 g) was stirred under nitrogen in 28.8 mL of tetrahydrofuran and treated dropwise with a solution of KN(SiMe$_3$)$_2$ in tetrahydrofuran (5.76 mL of a 1N solution). The bright orange solution was stirred at room temperature for 10 minutes, then cooled to −78° C. and treated dropwise with a solution of cis-1-ethyl-2,3,4,9-tetrahydro-4-(2-oxoethyl)-8-methyl-1H-carbazole-1-acetic acid methyl ester (4.43 mmol, 1.45 g) in 4.43 mL of tetrahydrofuran. The reaction mixture was allowed to warm to room temperature gradually over 1 hour, then it was diluted with 50 mL of 1:1 ether/petroleum ether, poured into 130 mL of water and extracted with 4×50 mL of 1:1 ether/petroleum ether. The pooled extracts were dried over magnesium sulfate and concentrated. Flash chromatography (75 mm diameter column, 10% ethyl acetate in petroleum ether eluent) afforded 1.81 g of a yellow oil. This was then refluxed under nitrogen for 45 minutes in a solution of ethanol (14.2 mL) and 2.5N NaOH (3.6 mL). The ethanol was then removed in vacuo and the residue was treated with 120 mL of 1N HCl. It was extracted with 4×50 mL of ether and dried over MgSO$_4$. Flash chromatography (50 mm diameter column, 2% H$_3$PO$_4$ in methanol treated silica gel, 8% EtOAc in petroleum ether eluent) afforded 1.46 g (4.15 mmol, 94%) of a pale yellow solid. Recrystallization from benzene/petroleum ether (15:85) afforded 900 mg of a white flocculent solid which was dried in vacuo at 69° C. over silica dessicant for 8 hours, m.p. 97.5°–98.5° C.

$^1$H NMR (CDCl$_3$, 400 MHz): δ 0.92 (t, 3H, J=7.5 Hz), 1.66–2.1 (m, 6H), 2.3–2.4 (m, 1H), 2.48 (s, 3H), 2.68–2.77 (m, 1H), 2.79 (s, 2H), 2.87 (broad t, 2H, J=6.2 Hz), 3.02–3.1 (m, 1H), 4.98–5.1 (m, 2H), 5.48–5.64 (m, 2H), 5.8–5.9 (m, 1H), 6.96 (d, 1H, J=7.1 Hz), 7.02 (t, 1H, J=7.4 Hz), 7.46 (d, 1H, J=7.7 Hz), 8.88 (s, 1H), 10.9–11.4 (broad s).

IR (KBr, cm$^{-1}$): 3420, 3050, 3010, 2970, 2930, 2890, 2870, 1705, 1680.

Anal. Calcd. for C$_{23}$H$_{29}$NO$_2$: C, 78.59; H, 8.32; N, 3.98; Found: C, 78.89; H, 8.29; N, 4.24.

We claim:

1. A compound of the formula (II)

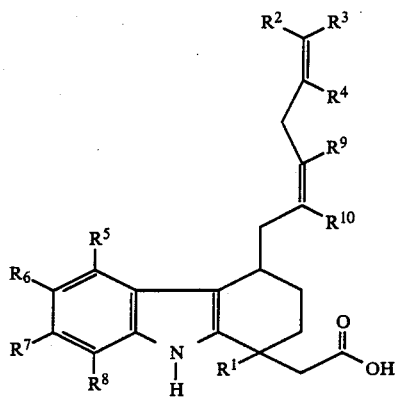

wherein $R^1$ is lower alkyl containing 1 to 6 carbon atoms and $R^2$, $R^3$ and $R^4$ are independently H, lower alkyl containing 1 to 6 carbon atoms or $R^3$ and $R^4$ are joined to form

or $(CH_2)_n$ wherein n is 3 to 5 $R^5$, $R^6$, $R^7$ and $R^8$ are independently H, lower alkyl containing 1 to 6 carbon atoms, halogen, haloalkyl; $R^9$ and $R^{10}$ are independently H, lower alkyl containing 1 to 6 carbon atoms or $R^9$ and $R^{10}$ are joined to form

3 to 5 or the pharmaceutically wherein m is pharmaceutically acceptable salts thereof.

2. A compound according to claim 1 of the formula (II) wherein $R^1$ is ethyl $R^2$, $R^3$, $R^4$, $R^5$, $R^6$, $R^7$, $R^9$, and $R^{10}$ are hydrogen; $R^8$ is methyl or ethyl or the pharmaceutically acceptable salts thereof.

3. A compound according to claim 2, [1α,4α(Z)]-1-ethyl-4-(2,5-hexadienyl)-2,3,4,9-tetrahydro-8-methyl-1H-carbazole-1-acetic acid or the pharmaceutically acceptable salts thereof.

4. A pharmaceutical composition comprising a compound of structure (II), or a pharmaceutically acceptable salt thereof, as defined in claim 1 and a pharmaceutically acceptable carrier.

5. A method for treating inflammatory or painful conditions in a mammal which comprises the administration to said mammal of an effective amount of a compound selected from those of formula (II), or a pharmaceutically acceptable salt thereof, as defined in claim 1.

* * * * *